United States Patent [19]
Nichtberger

[11] Patent Number: 6,136,804
[45] Date of Patent: Oct. 24, 2000

[54] COMBINATION THERAPY FOR TREATING, PREVENTING, OR REDUCING THE RISKS ASSOCIATED WITH ACUTE CORONARY ISCHEMIC SYNDROME AND RELATED CONDITIONS

[75] Inventor: Steven A. Nichtberger, Gladwyne, Pa.

[73] Assignee: Merck & Co., Inc., Rahway, N.J.

[21] Appl. No.: 09/267,287

[22] Filed: Mar. 12, 1999

Related U.S. Application Data

[60] Provisional application No. 60/077,900, Mar. 13, 1998.

[51] Int. Cl.[7] .......................... A61K 31/44; A01N 41/06; A01N 43/78
[52] U.S. Cl. .......................... 514/247; 514/165; 514/161; 514/162; 514/248; 514/249; 514/252; 514/253; 514/254; 514/332; 514/333; 514/334; 514/335; 514/354; 514/357; 514/367; 514/368; 514/378; 514/393; 514/394; 514/403; 514/406; 514/415; 514/424; 514/438; 514/468; 514/473; 514/534; 514/538; 514/540; 514/542; 514/551; 514/601; 514/602; 514/603; 514/605; 514/922; 514/301; 514/258
[58] Field of Search ...................... 514/165, 161, 514/162, 212, 213, 215, 247, 248, 249, 252, 253, 254, 258, 301, 332, 333, 334, 335, 354, 357, 367, 368, 378, 393, 394, 403, 406, 415, 424, 438, 468, 473, 534, 538, 540, 542, 551, 601, 602, 603, 605, 922

[56] References Cited

U.S. PATENT DOCUMENTS

| | | | |
|---|---|---|---|
| 5,292,756 | 3/1994 | Duggan et al. | 514/331 |
| 5,474,995 | 12/1995 | Ducharme et al. | 514/241 |
| 5,700,816 | 12/1997 | Isakson et al. | 514/326 |
| 5,800,385 | 9/1998 | Demopulos et al. | 604/49 |

FOREIGN PATENT DOCUMENTS

| | | |
|---|---|---|
| WO 97 14691 | 4/1997 | WIPO . |
| WO 98 03484 | 1/1998 | WIPO . |

OTHER PUBLICATIONS

Busch, U., et al., "Interaction of Meloxicam with Cimetidine, Maalox, or Aspirin," *J. Clin. Pharmacol.*, vol. 36, pp. 79–84 (1996).

Ridker, P. M., et al., "Inflammation, Aspirin, and the Risk of Cardiovascular Disease in Apparently Healthy Men," The New England Journal of Medicine, vol. 336, No. 14, (1997) pp. 973–979.

Talley, J. J., "Pulmonary–Allergy, Dermatological, Gastrointestinal & Arthritis—Selective Inhibitors of Cyclooxygenase–2," Exp. Opin. Ther. Patents, 7(1), (1997) pp. 55–62.

"Use of a Monoclonal Antibody Directed Against the Platelet Glycoprotein IIb/IIIa Receptor in . . . ," The New England Journal of Medicine, vol. 330, No. 14, pp. 956–961 (1994).

*Primary Examiner*—Frederick Krass
*Attorney, Agent, or Firm*—Richard S. Parr; Melvin Winokur

[57] ABSTRACT

The invention provides a method for treating, preventing, or reducing the risk of developing a condition selected from the group consisting of acute coronary ischemic syndrome, thrombosis, thromboembolism, thrombotic occlusion and reocclusion, restenosis, transient ischemic attack, and first or subsequent thrombotic stroke, in a patient, comprising administering to the patient a therapeutically effective amount of an antiplatelet agent in combination with a therapeutically effective amount of a COX-2 inhibitor. The invention also provides a pharmaceutical composition comprising a therapeutically effective amount of a COX-2 inhibitor, or a pharmaceutically acceptable salt thereof, and an antiplatelet agent, or a pharmaceutically acceptable salt thereof.

15 Claims, No Drawings

COMBINATION THERAPY FOR TREATING, PREVENTING, OR REDUCING THE RISKS ASSOCIATED WITH ACUTE CORONARY ISCHEMIC SYNDROME AND RELATED CONDITIONS

This application claims the benefit of Provisional Application No. 60/077,900, filed Mar. 13, 1998.

BACKGROUND OF THE INVENTION

Platelet activation and aggregation are involved in unstable angina and acute myocardial infarction, in reocclusion following thrombolytic therapy and angioplasty, in transient ischemic attacks and in a variety of other vasoocclusive disorders. When a blood vessel is damaged either by acute intervention such as angioplasty, or more chronically by the pathophysiological processes of atherosclerosis, platelets are activated to adhere to the disrupted surface and to each other. This activation, adherence and aggregation may lead to occlusive thrombus formation in the lumen of the blood vessel.

Antiplatelet therapy has been used in a wide variety of cardiovascular disease states and in conjunction with interventional therapy such as coronary artery or peripheral bypass grafting, cardiac valve replacement, and percutaneous transluminal coronary angioplasty (PTCA). Available drugs, such as aspirin and ticlopidine (TICLID®), have shown efficacy in syndromes involving vascular occlusion, presumably due to sustained inhibition of platelet function. However, the inhibitory effects of aspirin and ticlopidine are dependent upon the agonist which activates the platelet. For example, aspirin is effective in blocking platelet aggregation induced by agonists such as collagen that are dependent upon the cyclooxygenase pathway. It is, however, less effective against concentrations of thrombin which can act by cyclooxygenase independent pathways. Likewise, the inhibitory effects of ticlopidine, which inhibits ADP induced platelet aggregation, can be overcome by combinations of agonists. Thus, an efficacious platelet aggregation therapy that acts independently of the agonist and the pathway activating the platelet could be an important therapeutic advance giving greater efficacy than aspirin or ticlopidine alone in a broader spectrum of thrombotic events.

Integrin Superfamily

The firm attachment of endothelial cells to the subendothelial extracellular matrix is mediated via CAMs, which serve as receptors recognizing an array of adhesive proteins in the extracellular matrix. These proteins include von Willebrand factor (vWf), fibronectin, vitronectin, thrombospondin, laminins, collagen fibrils, elastin, microfibrils of elastin, and glycosaminoglycans. Most of the matrix adhesive molecules are the ligands for integrin receptors expressed in endothelial cells.

Integrins constitute an extended family ("superfamily") of membrane receptors interacting with adhesive proteins in plasma and extracellular matrix and with other membrane receptors (counter-receptors). The name "integrin" implies that they integrate the ligands on the outside of the cell with the cytoskeletal apparatus in the inside of the cell. Integrin receptors consist of a noncovalently linked $Ca^{2+}$-dependent, heterodimeric glycoprotein complex composed of $\alpha$ and $\beta$ subunits. The eight known integrin $\beta$ subunits give rise to eight families in which one "founder" $\beta$ subunit forms heterodimers with different $\alpha$ subunits. There are at least 14 known $\alpha$ subunits. Receptors belonging to the $\beta_1$ and $\beta_3$ families are expressed in endothelial cells. The $\beta_1$ family, also named Very Late Antigens (VLA), is represented by the fibronectin receptor ($\alpha_5\beta_1$, or VLA-5), the collagen receptor ($\alpha_2\beta_1$, or VLA-2) and the laminin receptor ($\alpha_6\beta_1$). The $\beta_3$ family is represented by the vitronectin receptor ($\alpha_v\beta_3$), which is structurally similar (the same $\beta_3$ subunit) to the platelet integrin receptor for fibrinogen, glycoprotein (GP) IIb/IIIa complex (also referred to as $\alpha_{IIb}\beta_3$). The functional difference between these two receptors is that the platelet receptor recognizes the g chain domain (HHLGGAKQAGDV) of human fibrinogen and the endothelial vitronectin receptor does not. Both recognize the sequence R-G-D identified as the cell adhesion site of fibronectin, vitronectin, vWf, and the a chain of human fibrinogen. Therefore, synthetic peptides containing the R-G-D sequence cause detachment of endothelial cells from the extracellular in matrix in vitro.

GP IIb/IIIa Antagonists

The final obligatory step in platelet aggregation is the binding of fibrinogen to an activated membrane-bound glycoprotein complex, GP IIb/IIIa. Platelet activators such as thrombin, collagen, epinephrine or ADP, are generated as an outgrowth of tissue damage. During activation, GP IIb/IIIa undergoes changes in conformation that results in exposure of occult binding sites for fibrinogen. There are six putative recognition sites within fibrinogen for GP IIb/IIIa and thus fibrinogen can potentially act as a hexavalent ligand to crossing GP IIb/IIIa molecules on adjacent platelets. A deficiency in either fibrinogen or GP IIb/IIIa prevents normal platelet aggregation regardless of the agonist used to activate the platelets. Since the binding of fibrinogen to its platelet receptor is an obligatory component of normal aggregation, GP IIb/IIIa is an attractive target for an antithrombotic agent.

Results from clinical trials of GP IIb/IIIa inhibitors support this hypothesis. The monoclonal antibody 7E3, which blocks the GP IIb/IIIa receptor, has been shown to be an effective therapy for the high risk angioplasty population. It is used as an adjunct to percutaneous transluminal coronary angioplasty or atherectomy for the prevention of acute cardiac ischemic complications in patients at high risk for abrupt closure of the treated coronary vessel. Although 7E3 blocks both the IIb/IIIa receptor and the $\alpha_v\beta_3$ receptor, its ability to inhibit platelet aggregation has been attributed to its function as a IIb/IIIa receptor binding inhibitor.

A study reported in The New England Journal of Medicine vol. 330, No. 14, pp. 956–961(1994) showed a decrease from 12.8% to 8.3% in the combined endpoints of death, non-fatal myocardial infarction (MI) and need for urgent revascularization with fibrinogen receptor blockade. This benefit was at the expense of some additional risk of bleeding, with the need for transfusion increasing from 3% to 6%, and the incidence of patients with decreased hematocrit increasing from 7% to 15%. 7E3 was added to the standard regime of heparin and aspirin thus leaving few hemostatic control mechanisms intact. The clinical benefits of this drug could be seen at 6 months.

Many other studies have shown that blocking the GPIIb/IIIa receptor will stop platelet aggregation induced by all of the agonists and thus prevent thrombus formation but leave platelet adhesion relatively intact. The 7E3 monoclonal antibody is described in Coller et al., *Ann. NY Acad. Sci.* 1991; 614:193–213; and Coller et al., *J. Clin Invest.* 1985; 76:101–108. Others have used agents based on the RGD sequence, including snake venom proteins, small peptides, and peptidomiimetics (Cook et al., *Drugs of Future*, 1994; 19:135–159; and Cox et al., *Medicinal Research Reviews,* 1994; 14:195–228).

The snake venom proteins, termed disintegrins, have provided important structural information, but their antigenicity has limited their development as therapeutic agents (Cook et al., ibid.; and Cox et al., ibid.). Integrelin (also known as INTEGRILIN™) is a cyclic peptide that is based on the KGD sequence in the snake venom protein barbourin (Cook et al., ibid.; and Cox et al., ibid.). It inhibits ligand binding to GP IIb/IIIa but has very little effect on ligand binding to $\alpha_v\beta_3$. Among the non-peptide compounds are Ro 44-9883 and MK-383, which are administered intravenously, and are also selective for GPIIb/IIIa (Cook et al., ibid.; and Cox et al., ibid.). Orally active agents include SC54684, which is a prodrug (i.e., it requires biotransformation in vivo to its active form) with high oral bioavailability and Ro 43-8857, GR144053, and DMP728, which are themselves the active inhibitors (Cook et al., ibid.; and Cox et al., ibid.). Literally thousands of other compounds have been synthesized in an attempt to obtain optimal potency, metabolic stability, receptor specificity, and favorable intravascular survival. Despite variations in these compounds, virtually of all of them when they are in their active form retain the basic charge relations of the RGD sequence with a positive charge separated from a negative charge by approximately 10–20 Å (Cook et al., ibid.; and Cox et al., ibid.).

Platelet aggregation is profoundly inhibited when increasing concentrations of murine 7E3 or c7E3 Fab are added to platelet-rich plasma in vitro or administered in incremental doses to animals or humans in vivo (Coller et al., *Ann. NY Acad.*, ibid.; Tcheng et al., ibid.; and Simoons et al., *Circulation* 1994; 89:596–603). There is an excellent correlation between the percentage of receptors blocked and the inhibition of aggregation, with nearly complete inhibition of aggregation when 80% or more of the receptors are blocked (Coller et al., *Ann. NY Acad.*, ibid.).

The results of the 7E3 study support the hypothesis that blockade of GPIIb/IIIa receptors is more effective than aspirin in preventing platelet thrombi, even in the presence of heparin. They also support the hypothesis that platelet-dependent thrombi frequently contribute significantly to the development of ischemic complications after PTCA, even when minor mechanical dissections are present.

COX-2 Inhibitors

Inhibitors of cyclooxygenase-2 are a sub-class of the class of drugs known as non-steroidal antiinflammatory drugs (NSAIDs). The NSAIDs are active in reducing the prostaglandin-induced pain and swelling associated with the inflammation process but are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandin by inhibiting enzymes in the human arachidonic acid/prostaglandin pathway including the enzyme cyclooxygenase (COX). The recent discovery that there are two isoforms of the COX enzyme, the first, COX-1, being involved with physiological functions and the second, COX-2, being induced in inflamed tissue, has given rise to a new approach. While conventional NSAIDs block both forms of the enzyme, the identification of the inducible COX-2 enzyme associated with inflammation has provided a viable target of inhibition which more effectively reduces inflammation and produces fewer and less drastic side effects. Many compounds which have activity as COX-2 inhibitors have been identified, and much research continues in this area.

Recently, a study published in N. Eng. J. Med. (Apr. 3, 1997) found that after several years of low-level inflammation, men are three times as likely to suffer heart attacks and twice as likely to have strokes. The study evaluated 1,086 men with levels of the C-reactive protein considered to be within normal range. Researchers found that those whose levels were in the upper 25% of the group were three times more likely to have suffered a heart attack more than six years later, and twice as likely to have a stroke than those whose levels were in the lowest 25%. Aspirin's benefits were particularly pronounced in the group with highest levels of the protein, suggesting that its anti-inflammatory effects were responsible for reduction in heart attacks and strokes.

Improved treatments for inhibiting platelet aggregation are currently being sought for the large number of individuals who are at risk for reocclusion following thrombolytic therapy and angioplasty, transient ischemic attacks and a variety of other vaso-occlusive disorders. The instant invention addresses this problem by providing a combination therapy comprised of an antiplatelet agent, and more particularly, a GP IIa/IIIb receptor antagonist, with a COX-2 inhibitor. When administered as part of a combination therapy, the COX-2 inhibitor together with the antiplatelet agent provide enhanced treatment options as compared to administration of either the antiplatelet agent or the COX-2 inhibitor alone.

SUMMARY OF THE INVENTION

The instant invention provides a novel drug combination comprised of an antiplatelet agent in combination with a COX-2 inhibitor, which is useful for inhibiting platelet aggregation in mammals.

The instant invention further provides novel methods for treating, preventing and reducing the risk of occurrence of acute coronary ischemic syndrome, including first or subsequent Q-wave myocardial infarction or angina pectoris, thrombosis, thromboembolism, thrombotic occlusion and reocclusion, restenosis, transient ischemic attack, and first or subsequent thrombotic stroke. Another object of this invention is to provide pharmaceutical compositions which can be used with the above-described methods. A further object is to provide a kit comprised of a COX-2 inhibitor composition and an antiplatelet agent composition. Additional objects will be evident from the following detailed description.

DETAILED DESCRIPTION OF THE INVENTION

The instant invention involves a novel combination therapy comprising the administration of a therapeutically effective amount of a COX-2 inhibitor in combination with a therapeutically effective amount of an antiplatelet agent to a mammal, and more particularly, to a human. The combination therapy is used to inhibit platelet aggregation in mammals who are in need of such inhibition, to inhibit inflammation in the vessels of mammals who are in need of such inhibition, and to prevent or treat disorders related to platelet aggregation.

The instant invention also provides pharmaceutical compositions comprised of a therapeutically effective amount of a COX-2 inhibitor, or a pharmaceutically acceptable salt thereof, in combination with a therapeutically effective amount of an antiplatelet agent, or a pharmaceutically acceptable salt thereof, and a pharmaceutically acceptable carrier. One embodiment of the instant compositions is a single composition adapted for oral administration comprised of a therapeutically effective amount of a COX-2 inhibitor in combination with a therapeutically effective amount of an antiplatelet agent and a pharmaceutically acceptable carrier. The combination can also be administered in separate dosage forms, each having one of the active agents. If administered in separate dosage forms, the separate dosage forms are administered such that the beneficial effect of each active agent is realized by the patient at substantially the same time.

"Pharmaceutically acceptable salts" means non-toxic salts of the compounds employed in this invention which are generally prepared by reacting the free acid with a suitable organic or inorganic base. Examples of salt forms of antiplatelet agents may include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, potassium, salicylate, sodium, stearate, subacetate, succinate, tannate, tartrate, teoclate, tosylate, triethiodide, and valerate. Examples of salt forms of COX-2 inhibitors include but are not limited to salts derived from inorganic bases including aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

"Acute coronary ischemia" refers to local anemia due to mechanical obstruction, e.g. arterial narrowing, of the blood supply. The condition is also referred to as myocardial ischemia and is characterized by inadequate circulation of blood to the myocardium, usually as a result of coronary artery disease. Ischemia of the heart muscle is evidenced by a pain in the chest often radiating from the precordium to the left shoulder and down the arm (angina pectoris) and is caused by coronary disease. Ischemia also includes myocardial infarction, which results from occlusion of a coronary artery. As used herein, the term "myocardial infarction" is intended to include both Q-wave and non-Q-wave myocardial infarction, unless otherwise noted.

"Inhibitor of cyclooxygenase-2", "cyclooxygenase-2 inhibitor" and "COX-2 inhibitor" as used herein embrace compounds which selectively inhibit cyclooxygenase-2 over cyclooxygenase-1.

"Therapeutically effective amount" means that amount of a drug or pharmaceutical agent that will elicit the biological or medical response of a tissue, a system, animal or human that is being sought by a researcher, veterinarian, medical doctor or other clinician.

"Prophylactically effective amount" means that amount of a pharmaceutical drug that will prevent or reduce the risk of occurrence of the biological or medical event that is sought to be prevented in a tissue, a system, animal or human by a researcher, veterinarian, medical doctor or other clinician.

"Reducing the risk" or "reduction of risk" of occurrence of conditions selected from acute coronary ischemic syndrome, including first or subsequent Q-wave myocardial infarction or angina pectoris, thrombosis, thromboembolism, thrombotic occlusion and reocclusion, restenosis, transient ischemic attack, and first or subsequent thrombotic stroke refers to lowering the risk occurrence of any of the above conditions in a patient at risk to developing the conditions. Patients at risk to developing the conditions include those having a history of heart disease, a family history of heart disease, a genetic predisposition to developing the conditions, diabetes, hypercholesteremia, hypertension, and smokers.

The term "patient" includes mammals, especially humans, who take an antiplatelet agent in combination with a COX-2 inhibitor for any of the uses described herein.

"Cerebrovascular ischemic events" are those relating to reduced blood supply to the brain, and include but are not limited to first or subsequent thrombotic strokes, or transient ischemic attacks.

Ester derivatives of the described compounds may act as prodrugs which, when absorbed into the bloodstream of a warm-blooded animal, may cleave in such a manner as to release the drug form and permit the drug to afford improved therapeutic efficacy.

COX-2 Inhibitors

Employing the human whole blood COX-1 assay and the human whole blood COX-2 assay described in C. Brideau et al, *Inflamm. Res.* 45: 68–74 (1996), herein incorporated by reference, preferably, the compounds have a cyclooxygenase-2 $IC_{50}$ of less than about 2 $\mu$M in the human whole blood COX-2 assay, yet have a cyclooxygenase-1 $IC_{50}$ of greater than about 5 $\mu$M in the human whole blood COX-1 assay. Also preferably, the compounds have a selectivity ratio of cyclooxygenase-2 inhibition over cyclooxygenase-1 inhibition of at least 10, and more preferably of at least 40. The resulting selectivity may indicate an ability to reduce the incidence of common NSAID-induced side effects.

The inhibitor of cyclooxygenase-2 may be administered at a dosage level up to conventional dosage levels for NSAIDs. Suitable dosage levels will depend upon the antiinflammatory effect of the chosen inhibitor of cyclooxygenase-2, but typically suitable levels will be about 0.001 to 50 mg/kg per day, preferably 0.005 to 30 mg/kg per day, and especially 0.05 to 10 mg/kg per day. The compound may be administered on a regimen of up to 6 times per day, preferably 1 to 4 times per day, and especially once per day.

As explained in J. Talley, *Exp. Opin. Ther. Patents* (1997), 7(1), pp. 55–62, three distinct structural classes of selective COX-2 inhibitor compounds have been identified. One class is the methane sulfonanilide class of inhibitors, of which NS-398, flosulide, nimesulide and (i) are example members.

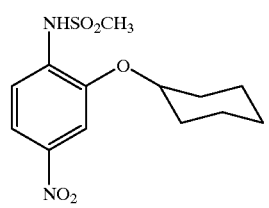

NS-398

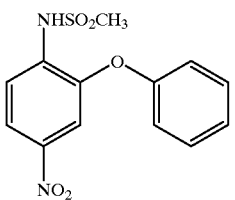

Nimesulide

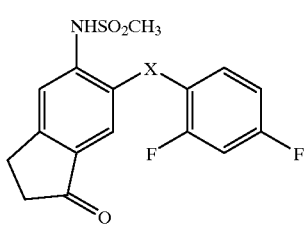

(i), X = S
Flosulide, X = O

A second class is the tricyclic inhibitor class, which can be further divided into the sub-classes of tricyclic inhibitors with a central carbocyclic ring (examples include SC-57666, 1 and 2; those with a central monocyclic heterocyclic ring (examples include DuP 697, SC-58125, SC-58635, and 3, 4 and 5); and those with a central bicyclic heterocyclic ring (examples include 6, 7, 8, 9 and 10). Compounds 3, 4 and 5 are described in U.S. Pat. No. 5,474,995.

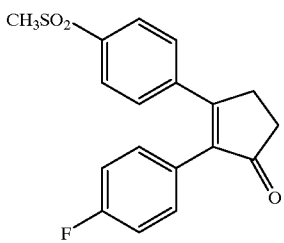

SC-57666

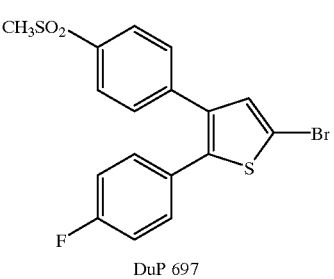

1

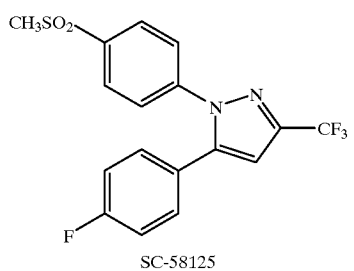

2

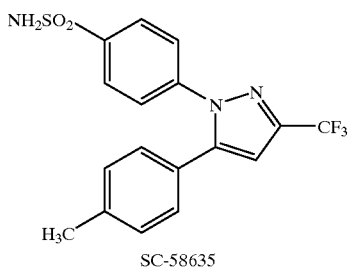

DuP 697

SC-58125

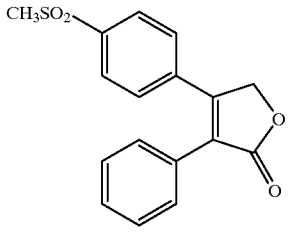

SC-58635

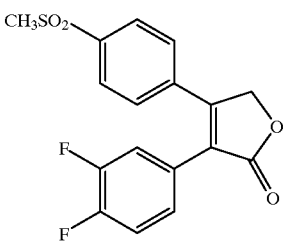

3

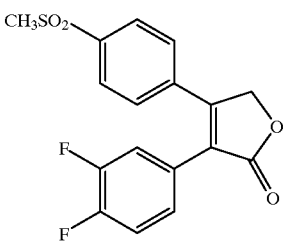

4

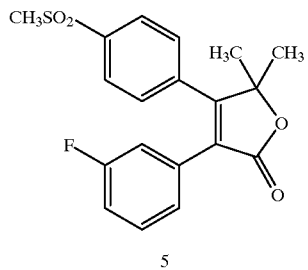

5

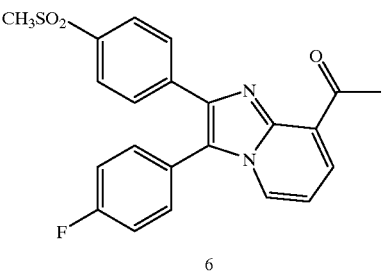

6

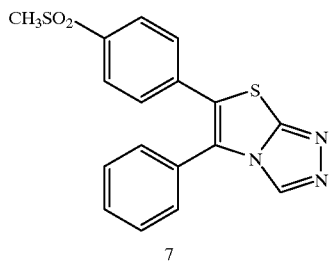

7

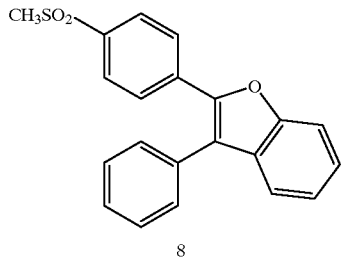

8

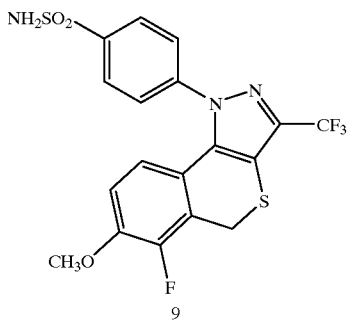

9

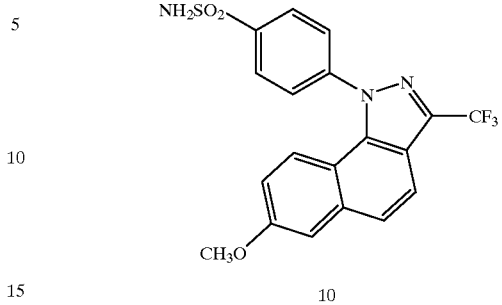

10

The third identified class can be referred to as those which are structurally modified NSAIDS, and includes 11a and structure 11 as example members.

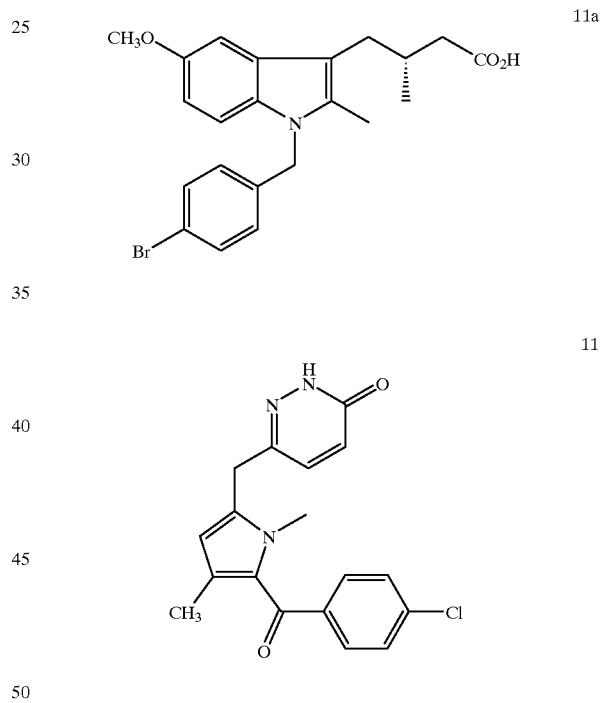

In addition to the structural classes, sub-classes, specific COX-2 inhibitor compound examples, and reference journal and patent publications described in the Talley publication which are all herein incorporated by reference, examples of compounds which selectively inhibit cyclooxygenase-2 have also been described in the following patent publications, all of which are herein incorporated by reference: U.S. Pat. Nos. 5,344,991, 5,380,738, 5,393,790, 5,409,944, 5,434,178, 5,436,265, 5,466,823, 5,474,995, 5,510,368, 5,536,752, 5,550,142, 5,552,422, 5,604,253, 5,604,260, 5,639,780; and International Patent Specification Nos. 94/13635, 94/15932, 94/20480, 94/26731, 94/27980, 95/00501, 95/15316, 96/03387, 96/03388, 96/06840; and International Publication No.'s WO 94/20480, WO 96/21667, WO 96/31509, WO 96/36623, WO 97/14691, WO 97/16435.

Additional COX-2 inhibitor compounds which are included in the scope of this invention include:
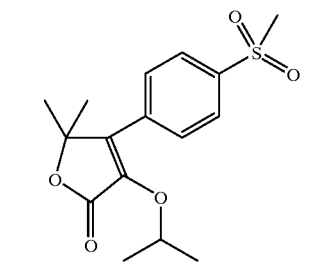
12
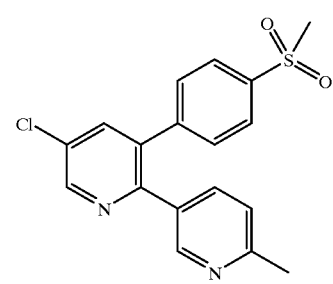
13
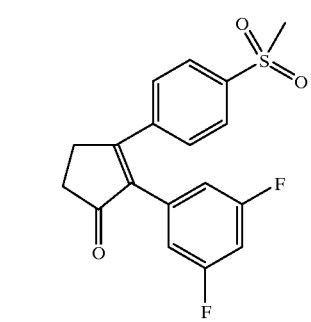
14
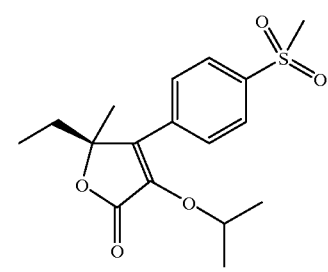
15
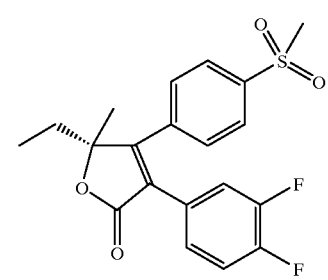
16
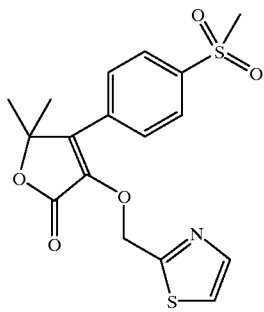
17
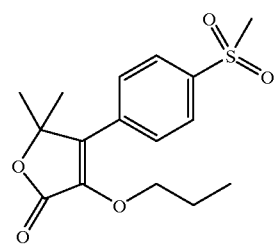
18
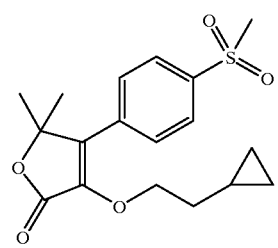
19
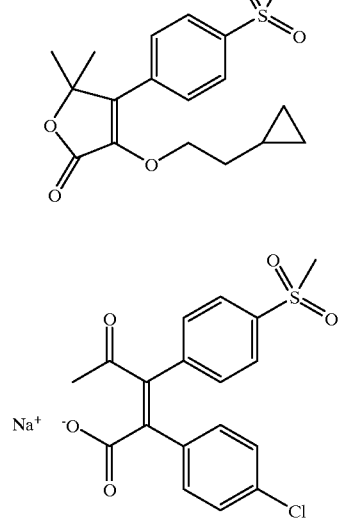
20
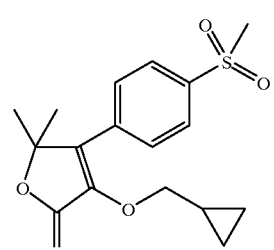
21

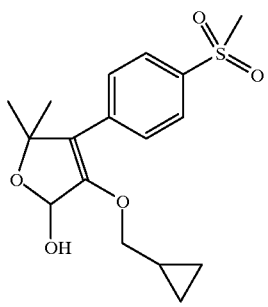

22

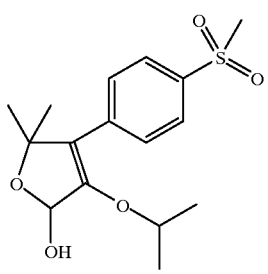

23

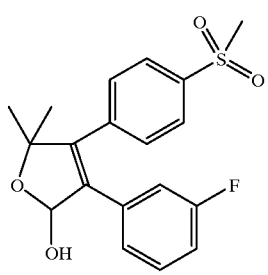

24

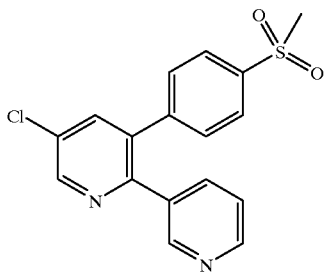

25

Some of the compounds above can also be identified by the following chemical names:

3: 3-phenyl-4-(4-(methylsulfonyl)phenyl)-2-(5H)-furanone;
4: 3-(3,4-difluorophenyl)-4-(4-(methylsulfonyl)phenyl)-2-(5H)-faranone;
5: 5,5-dimethyl-4-(4-methylsulfonyl)phenyl)-3-(3-fluorophenyl)-H-furan-2-one;
12: 5,5-dimethyl-4-(4-(methylsulfonyl)phenyl)-3-(2-propoxy)-5H-furan-2-one;
13: 5-chloro-3-(4-(methylsulfonyl)phenyl)-2-(2-methyl-5-pyridinyl)pyridine;
14: 2-(3,5-difluorophenyl)-3-(4-(methylsulfonyl)phenyl)-2-cyclopenten-1-one;
15: 5(S)-5-ethyl-5-methyl-4-(4-(methylsulfonyl)phenyl)-3-(2-propoxy)-5H-furan-2-one;
16: 5-ethyl-5-methyl-4-(4-(methylsulfonyl)phenyl)-3-(3,4-difluorophenyl)-5H-furan-2-one;
17: 3-((2-thiazolyl)methoxy)-4-(4-(methylsulfonyl)phenyl)-5,5-dimethyl-5H-furan-2-one;
18: 3-propyloxy-4-(4-(methylsulfonyl)phenyl)-5,5-dimethyl-5H-furan-2-one;
19: 3-(1-cyclopropylethoxy)-5,5-dimethyl-4-(4-methylsulfonyl)phenyl)-5H-furan-2-one;
20: sodium 2-(4-chlorophenyl)-3-(4-(methylsulfonyl) phenyl)-4-oxo-2-pentenoate;
21: 3-(cyclopropylmethoxy)-5,5-dimethyl-4-(4-(methylsulfonyl)phenyl)-5H-furan-2-one;
22: 3-(cyclopropylmethoxy)-5,5-dimethyl-4-(4-(methylsulfonyl)phenyl)-2,5-dihydrofuran-2-ol;
23: 3-isopropoxy-5,5-dimethyl-4-(4-(methylsulfonyl) phenyl)-2,5-dihydrofuran-2-ol;
24: 5,5-dimethyl-3-(3-fluorophenyl)-2-hydroxy-4-(4-(methylsulfonyl)phenyl)-2,5-dihydrofuran;
25: 5-Chloro-3-(4-(methylsulfonyl)phenyl)-2-(3-pyridinyl) pyridine.

The following publications describe and/or provide methods for making the compounds as indicated: compounds 12, 15, 17, 18, 19 and 21, WO 97/14691; compounds 22, 23 and 24, WO 97/16435; compound 20, WO 96/36623; compound 14, U.S. Pat. No. 5,536,752; compound 16, U.S. Pat. No. 5,474,995. See Examples herein for compounds 13 and 25.

Also incorporated herein by reference are those compounds described in WO 96/41645 as having structural Formula I, shown below, and the definition and preferred definitions and species described therein:

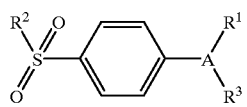

I

Particularly preferred compounds of formula (I) include:
5-(4-fluorophenyl)-1-[4-(methylsulfonyl)phenyl]-3-(trifluoromethyl)pyrazole;
4-(4-fluorophenyl)-5-[4-(methylsulfonyl)phenyl]-1-phenyl-3-(trifluoromethyl)pyrazole;
4-(5-(4-chlorophenyl)-3-(4-methoxyphenyl)-1H-pyrazol-1-yl)benzenesulfonamide;
4-(3,5-bis(4-methylphenyl)-1H-pyrazol-1-yl) benzenesulfonamide;
4-(5-(4-chlorophenyl)-3-phenyl-1H-pyrazol-1-yl) benzenesulfonamide;
4-(3,5-bis(4-methoxyphenyl)-1H-pyrazol-1-yl) benzenesulfonamide;
4-(5-(4-chlorophenyl)-3-(4-methylphenyl)-1H-pyrazol-1-yl)benzenesulfonamide;
4-(5-(4-chlorophenyl)-3-(4-nitrophenyl)-1H-pyrazol-1-yl)benzenesulfonamide;
4-(5-(4-chlorophenyl)-3-(5-chloro-2-thienyl)-1H-pyrazol-1-yl)benzenesulfonamide;
4-(4-chloro-3,5-diphenyl-1H-pyrazol-1-yl) benzenesulfonamide;
4-(5-(4-chlorophenyl)-3-(trifluoromethyl)-1H-pyrazol-1-yl)benzenesulfonamide;
4-(5-phenyl)-3-(trifluoromethyl)-1H-pyrazol-1-yl) benzenesulfonamide;
4-(5-(4-fluorophenyl)-3-(trifluoromethyl)-1H-pyrazol-1-yl)benzenesulfonamide;
4-(5-(4-methoxyphenyl)-3-(trifluoromethyl)-1H-pyrazol-1-yl)benzenesulfonamide;
4-(5-(4-chlorophenyl)-3-(difluoromethyl)-1H-pyrazol-1-yl)benzenesulfonamide;
4-(5-(4-methylphenyl)-3-(trifluoromethyl)-1H-pyrazol-1-yl)benzenesulfonamide;
4-(4-chloro-5-(4-chlorophenyl)-3-(trifluoromethyl)-1H-pyrazol-1-yl)benzenesulfonamide;
4-(3-(difluoromethyl)-5-(4-methylphenyl)-1H-pyrazol-1-yl)benzenesulfonamide;

4-(3-(difluoromethyl)-5-phenyl-1H-pyrazol-1-yl)benzenesulfonamide;
4-(3-(difluoromethyl)-5-(4-methoxyphenyl)-1H-pyrazol-1-yl)benzene sulfonamide;
4-(3-cyano-5-(4-fluorophenyl)-1H-pyrazol-1-yl)benzenesulfonamide;
4-(3-(difluoromethyl)-5-(3-fluoro-4-methoxyphenyl)-1H-pyrazol-1-yl)benzenesulfonamide;
4-(5-(3-fluoro-4-methoxyphenyl)-3-(trifluoromethyl)-1H-pyrazol-1-yl)benzenesulfonamide;
4-(4-chloro-5-phenyl-1H-pyrazol-1-yl)benzenesulfonamide;
4-(5-(4-chlorophenyl)-3-(hydroxyphenyl)-1H-pyrazol-1-yl)benzenesulfonamide;
4-(5-(4-(N,N-dimethylamino)phenyl)-3-(trifuoromethyl)-1H-pyrazol-1-yl)benzenesulfonamide;
5-(4-fluorophenyl)-6-(4-(methylsulfonyl)phenyl)spiro[2.4]hept-5-ene;
4-(6-(4-fluorophenyl)spiro[2.4]hept-5-en-5-yl)benzenesulfonamide;
6-(4-fluorophenyl)-7-(4-(methylsulfonyl)phenyl)spiro[3.4]oct-6-ene;
5-(3-chloro-4-methoxyphenyl)-6-(4-(methylsulfonyl)phenyl)spiro[2.4]hept-5-ene;
4-(6-(3-chloro-4-methoxyphenyl)spiro[2.4]hept-5-en-5-yl)benzenesulfonamide;
5-(3,5-dichloro-4-methoxyphenyl)-6-(4-(methylsulfonyl)phenyl)spiro[2.4]hept-5-ene;
5-(3-chloro-4-fluorophenyl)-6-(4-(methylsulfonyl)phenyl)spiro[2.4]hept-5-ene;
4-(6-(3,4-dichlorophenyl)spiro[2.4]hept-5-en-5-yl)benzenesulfonamide;
2-(3-chloro-4-fluorophenyl)-4-(4-fluorophenyl)-5-(4-methylsulfonylphenyl)thiazole;
2-(2-chlorophenyl)-4-(4-fluorophenyl)-5-(4-methylsulfonylphenyl)thiazole;
5-(4-fluorophenyl)-4-(4-methylsulfonylphenyl)-2-methylthiazole;
4-(4-fluorophenyl)-5-(4-methylsulfonylphenyl)-2-trifluoromethylthiazole;
4-(4-fluorophenyl)-5-(4-methylsulfonylphenyl)-2-(2-thienyl)thiazole;
4-(4-fluorophenyl)-5-(4-methylsulfonylphenyl)-2-benzylaminothiazole;
4-(4-fluorophenyl)-5-(4-methylsulfonylphenyl)-2-(1-propylamino)thiazole;
2-((3,5-dichlorophenoxy)methyl)-4-(4-fluorophenyl)-5-(4-(methylsulfonyl)phenyl)thiazole;
5-(4-fluorophenyl)-4-(4-methylsulfonylphenyl)-2-trifluoromethylthiazole;
1-methylsulfonyl-4-(1,1-dimethyl-4-(4-fluorophenyl)cyclopenta-2,4-dien-3-yl)benzene;
4-(4-(4-fluorophenyl-1,1-dimethylcyclopenta-2,4-dien-3-yl)benzenesulfonamide;
5-(4-fluorophenyl)-6-(4-(methylsulfonyl)phenyl)spiro[2.4]hepta-4,6-diene;
4-(6-(4-fluorophenyl)spiro[2.4]hepta-4,6-dien-5-yl)benzenesulfonamide;
6-(4-fluorophenyl)-2-methoxy-5-(4-(methylsulfonyl)phenyl)-pyridine-3-carbonitrile;
2-bromo-6-(4-fluorophenyl)-5-(4-(methylsulfonyl)phenyl)-pyridine-3-carbonitrile;
6-(4-fluorophenyl)-5-(4-(methylsulfonyl)phenyl)-2-phenyl-pyridine-3-carbonitrile;
4-(2-(4-methylpyridin-2-yl)-4-(trifluoromethyl)-1H-imidazol-1-yl)benzenesulfonamide;
4-(2-(5-methylpyridin-3-yl)-4-(trifluoromethyl)-1H-imidazol-1-yl)benzenesulfonamide;
4-(2-(2-methylpyridin-3-yl)-4-(trifluoromethyl)-1H-imidazol-1-yl)benzenesulfonamide;
3-(1-(4-(methylsulfonyl)phenyl)-4-(trifluoromethyl)-1H-imidazol-2-yl)benzenesulfonamide;
2-(1-(4-(methylsulfonyl)phenyl)-4-(trifluoromethyl)-1H-imidazol-2-yl)pyridine;
2-methyl-4-(1-(4-(methylsulfonyl)phenyl)-4-(trifluoromethyl)-1H-imidazol-2-yl)pyridine;
2-methyl-6-(1-(4-(methylsulfonyl)phenyl)-4-(trifluoromethyl)-1H-imidazol-2-yl)pyridine;
4-(2-(6-methylpyridin-3-yl)-4-(trifluoromethyl)-1H-imidazol-1-yl)benzenesulfonamide;
2-(3,4-difluorophenyl)-1-(4-(methylsulfonyl)phenyl)-4-(trifluoromethyl)-1H-imidazole;
4-(2-(4-methylphenyl)-4-(trifluoromethyl)-1H-imidazol-1-yl)benzenesulfonamide;
2-(4-chlorophenyl)-1-(4-(methylsulfonyl)phenyl)-4-methyl-1H-imidazole;
2-(4-chlorophenyl)-1-(4-(methylsulfonyl)phenyl)-4-phenyl-1H-imidazole;
2-(4-chlorophenyl)-4-(4-fluorophenyl)-1-(4-(methylsulfonyl)phenyl)-1H-imidazole;
2-(3-fluoro-4-methoxyphenyl)-1-(4-(methylsulfonyl)phenyl)-4-(trifluoromethyl)-1H-imidazole;
1-(4-(methylsulfonyl)phenyl)-2-phenyl-4-trifluoromethyl-1H-imidazole;
2-(4-methylphenyl)-1-(4-(methylsulfonyl)phenyl)-4-trifluoromethyl-1H-imidazole;
4-(2-(3-chloro-4-methylphenyl)-4-(trifluoromethyl)-1H-imidazol-1-yl)benzenesulfonamide;
2-(3-fluoro-5-methylphenyl)-1-(4-(methylsulfonyl)phenyl)-4-(trifluoromethyl)-1H-imidazole;
4-(2-(3-fluoro-5-methylphenyl)-4-(trifluoromethyl)-1H-imidazol-1-yl)benzenesulfonamide;
2-(3-methylphenyl)-1-(4-(methylsulfonyl)phenyl)-4-(trifluoromethyl)-1H-imidazole;
4-(2-(3-methylphenyl)-4-(trifluoromethyl)-1H-imidazol-1-yl)benzenesulfonamide;
1-(4-(methylsulfonyl)phenyl)-2-(3-chlorophenyl)-4-(trifluoromethyl)-1H-imidazole;
4-(2-(3-chlorophenyl)-4-(trifluoromethyl)-1H-imidazol-1-yl)benzenesulfonamide;
4-(2-phenyl-4-(trifluoromethyl)-1H-imidazol-1-yl)benzenesulfonamide;
4-(2-(4-methoxy-3-chlorophenyl)-4-(trifluoromethyl)-1H-imidazol-1-yl)benzenesulfonamide;
1-allyl-4-(4-fluorophenyl)-3-(4-(methylsulfonyl)phenyl)-5-(trifluoromethyl)-1H-pyrazole;
4-(1-ethyl-4-(4-fluorophenyl)-5-(trifluoromethyl)-1H-pyrazol-3-yl)benzenesulfonamide;
N-phenyl-(4-(4-fluorophenyl)-3-(4-(methylsulfonyl)phenyl)-5-(trifluoromethyl)-1H-pyrazol-1-yl)acetamide;
ethyl (4-(4-fluorophenyl)-3-(4-(methylsulfonyl)phenyl)-5-(trifluoromethyl)-1H-pyrazol-1-yl)acetate;
4-(4-fluorophenyl)-3-(4-(methylsulfonyl)phenyl)-1-(2-phenylethyl)-1H-pyrazole;
4-(4-fluorophenyl)-3-(4-(methylsulfonyl)phenyl)-1-(2-phenylethyl)-5-(trifluoromethyl)pyrazole;
1-ethyl-4-(4-fluorophenyl)-3-(4-(methylsulfonyl)phenyl)-5-(trifluoromethyl)-1H-pyrazole;
5-(4-fluorophenyl)-4-(4-(methylsulfonyl)phenyl)-2-(trifluoromethyl)-1H-imidazole;
4-(4-(methylsulfonyl)phenyl)-5-(2-thiophenyl)-2-(trifluoromethyl)-1H-imidazole;
5-(4-fluorophenyl)-2-methoxy-4-(4-(methylsulfonyl)phenyl)-6-(trifluoromethyl)pyridine;
2-ethoxy-5-(4-fluorophenyl)-4-(4-(methylsulfonyl)phenyl)-6-(trifluoromethyl)pyridine;
5-(4-fluorophenyl)-4-(4-(methylsulfonyl)phenyl)-2-(2-propynyloxy)-6-(trifluoromethyl)pyridine;
2-bromo-5-(4-fluorophenyl)-4-(4-(methylsulfonyl)phenyl)-6-(trifluoromethyl)pyridine;
4-(2-(3-chloro-4-methoxyphenyl)-4,5-difluorophenyl)benzenesulfonamide;
1-(4-fluorophenyl)-2-(4-(methylsulfonyl)phenyl)benzene;

5-difluoromethyl-4-(4-(methylsulfonyl)phenyl)-3-phenylisoxazole;
4-(3-ethyl-5-phenylisoxazol-4-yl)benzenesulfonamide;
4-(5-difluoromethyl-3-phenylisoxazol-4-yl)benzenesulfonamide;
4-(5-hydroxymethyl-3-phenylisoxazol-4-yl)benzenesulfonamide;
4-(5-methyl-3-phenylisoxazol-4-yl)benzenesulfonamide;
1-(2-(4-fluorophenyl)cyclopenten-1-yl)-4-(methylsulfonyl)benzene;
1-(2-(4-fluoro-2-methylphenyl)cyclopenten-1-yl)-4-(methylsulfonyl)benzene;
1-(2-(4-chlorophenyl)cyclopenten-1-yl)-4-(methylsulfonyl)benzene;
1-(2-(2,4-dichlorophenyl)cyclopenten-1-yl)-4-(methylsulfonyl)benzene;
1-(2-(4-trifluoromethylphenyl)cyclopenten-1-yl)-4-(methylsulfonyl)benzene;
1-(2-(4-methylthiophenyl)cyclopenten-1-yl)-4-(methylsulfonyl)benzene;
1-(2-(4-fluorophenyl)-4,4-dimethylcyclopenten-1-yl)-4-(methylsulfonyl)benzene;
4-(2-(4-fluorophenyl)-4,4-dimethylcyclopenten-1-yl)benzenesulfonamide;
1-(2-(4-chlorophenyl)-4,4-dimethylcyclopenten-1-yl)-4-(methylsulfonyl)benzene;
4-(2-(4-chlorophenyl)-4,4-dimethylcyclopenten-1-yl)benzenesulfonamide;
4-(2-(4-fluorophenyl)cyclopenten-1-yl)benzenesulfonamide;
4-(2-(4-chlorophenyl)cyclopenten-1-yl)benzenesulfonamide;
1-(2-(4-methoxyphenyl)cyclopenten-1-yl)-4-(methylsulfonyl)benzene;
1-(2-(2,3-difluorophenyl)cyclopenten-1-yl)-4-(methylsulfonyl)benzene;
4-(2-(3-fluoro-4-methoxyphenyl)cyclopenten-1-yl)benzenesulfonamide;
1-(2-(3-chloro-4-methoxyphenyl)cyclopenten-1-yl)-4-(methylsulfonyl)benzene;
4-(2-(3-chloro-4-fluorophenyl)cyclopenten-1-yl)benzenesulfonamide;
4-(2-(2-methylpyridin-5-yl)cyclopenten-1-yl)benzenesulfonamide;
ethyl 2-(4-(4-fluorophenyl)-5-(4-(methylsulfonyl)phenyl)oxazol-2-yl)-2-benzyl-acetate;
2-(4-(4-fluorophenyl)-5-(4-(methylsulfonyl)phenyl)oxazol-2-yl)acetic acid;
2-(tert-butyl)-4-(4-fluorophenyl)-5-(4-(methylsulfonyl)phenyl)oxazole;
4-(4-fluorophenyl)-5-(4-(methylsulfonyl)phenyl)-2-phenyloxazole;
4-(4-fluorophenyl)-2-methyl-5-(4-(methylsulfonyl)phenyl)oxazole; and
4-(5-(3-fluoro-4-methoxyphenyl)-2-trifluoromethyl-4-oxazolyl)benzenesulfonamide;
or a pharmaceutically acceptable salt thereof.

Antiplatelet Agents

Antiplatelet agents suitable for use in the present invention include glycoprotein IIb/IIIa receptor antagonists, clopidogrel, ticlopidine, dipyridamole and aspirin.

Glycoprotein IIb/IIIa receptor antagonists inhibit the binding of fibrinogen to the IIb/IIIa platelet receptor site, thereby inhibiting platelet aggregation. Examples of glycoprotein IIb/IIIa receptor antagonists are described in U.S. Pat. Nos. 5,470,849, 5,463,011, 5,455,243, 5,451,578, 5,446,056, 5,441,952, 5,422,249, 5,416,099, 5,405,854, 5,397,791, 5,393,760, 5,389,631, 5,380,713, 5,374,622, 5,358,956, 5,344,783, 5,340,798,5,338,723, 5,334,596, 5,321,034, 5,318,899 (e.g. cyclic heptapeptides such as Mpr-(Acetimidyl-Lys)-Gly-Asp-Trp-Phe-Cys-$NH_2$, Mpr-(Acetimidyl-Lys)-Gly-Asp-Trp-Phe-Pen-$NH_2$, Mpr-(Phenylimidyl-Lys)-Gly-Asp-Trp-Phe-Pen-$NH_2$, and Mpr-(Phenylimidyl-Lys)-Gly-Asp-Trp-Phe-Cys-$NH_2$, wherein Mpr is mercapto propionyl), U.S. Pat. Nos. 5,312,923, 5,294,616, 5,292,756 (which includes tirofiban), U.S. Pat. Nos. 5,281,585, 5,272,158, 5,264,420,5,260,307, 5,239,113 (e.g. ethyl 3-[[4-[[4-(aminoiminomethyl)phenyl]amino]-1,4-dioxobutyl]amino]-4-pentynoate), U.S. Pat. Nos. 5,227,490, 5,206,373, 4,703,036 (e.g. N-Methyl-D-phenylalanyl-N-[(1S)-1-formyl-4-guanidinobutyl]-L-prolinamide); European Patent publication No.'s EP 505 868 (e.g., ((1-(2-((4-(aminoiminomethyl)benzoyl)amino)-3-(4-hydroxyphenyl)-1-oxopropyl)-4-piperidinyl)oxy)-(S)-acetic acid), EP 333 356, and EP 656 348; and International Publication No.'s WO 93/11152 (e.g., N-(2-(2-(((3-((aminoiminomethyl)amino)propyl)amino)-carbonyl)-1-piperidnyl)-1-(cyclohexylmethyl)-2-oxoethyl)-(R,S)-glycine), WO 94/18981, WO 94/22820, WO 95/14683, and WO 97/15568, all of which are herein incorporated by reference, and wherein the scope of this invention includes, but is not limited to, the use of each of the specifically disclosed compounds therein. They are described as useful for inhibiting fibrinogen binding and inhibiting clot formation.

In particular, the GP IIb/IIIa receptor antagonist is selected from the following compounds and the pharmaceutically acceptable salts, esters, and solvates (including hydrates) thereof: [3(R)-[2-piperidin-4-yl)ethyl]-2-piperidone-1]acetyl-3(R)-methyl-β-alanine described in U.S. Pat. No. 5,281,585, (see compound 57 in column 67) and referred to herein as Compound A:

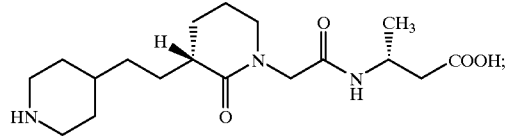

Compound A

5-[(4-Piperidinyl)methoxy]-2-indolecarbonyl-2(S)-phenylsulfonyl-amino-β-alanine described in WO 97/15568 at page 20 as compound 2-6, and referred to herein as Compound B:

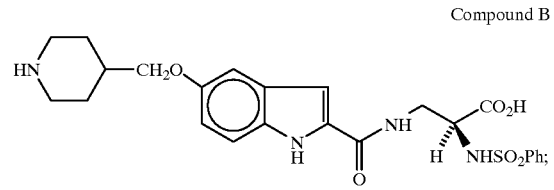

Compound B

2(S)-[(p-Toluenesulfonyl)amino]-3-[[[5,6,7,8-tetrahydro-4-oxo-5-[2-(piperidin-4-yl)ethyl]-4H-pyrazolo-[1,5-α][1,4]diazepin-2-yl]carbonyl]-amino]propionic acid described in WO 94/18981, and referred to herein as Compound C:

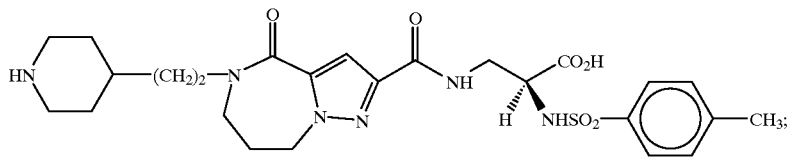

Compound C

MK-383 (2-S-(n-Butylsulfonylamino)-3[4-piperidin-4-yl)butyloxyphenyl]propionic acid hydrochloride, and also known as tirofiban) described in U.S. Pat. No. 5,292,756; DMP 728; DMP 754 ((R)-methyl-3-[[[3-[4-(aminoiminomethyl)phenyl]-4,5-dihydro-5-isoxazolyl]acetyl]amino]-N-(butoxycarbonyl)-L-alanine monoacetate) from DuPont-Merck, described in WO 95/14683 and in *Tetrahedron Letters*, 1996,37:4455–4458:

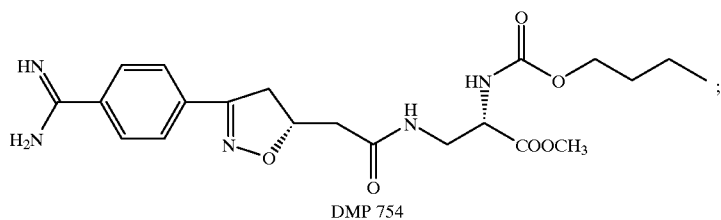

DMP 754

Ro44-9883, Ro43-8857 and Ro48-3657 (acetic add, [[1-[2-[[4-[amino(hydroxyimino)methyl]benzoyl]amino]-1-oxopropyl]-4-piperidinyl]oxy]-, ethyl ester, and also known as sibrafiban) from Hoffman-LaRoche; sibrafiban and related compounds are described in EP 656 348:

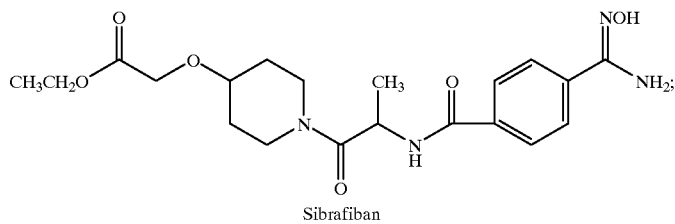

Sibrafiban xemlofiban (ethyl 3-[[4-[[4-(aminoiminomethyl)phenyl]amino]-1,4-dioxobutyl]amino]-4-pentynoate, also known as xemilofiban and SC-54684), particularly the HC salt thereof, described in U.S. Pat. Nos. 5,344,957 and 5,239,113:

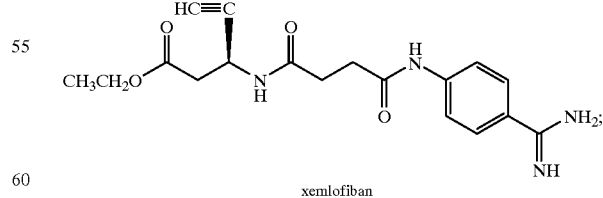

xemlofiban fradafiban ((3S,5S)-5-[[(4'-Amidino-4-biphenyl)oxy]methyl]-2-oxo-3-pyrrolidineacetic acid, also known as BIBU-104) as described in U.S. Pat. No. 5,541,343 assigned to Thomae:

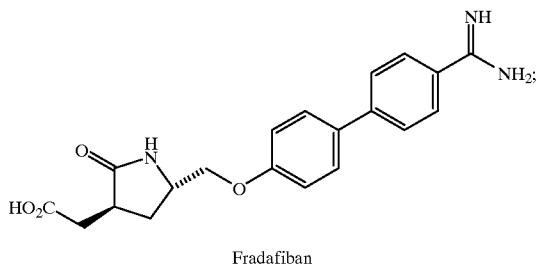

Fradafiban

Fradafiban orbofiban (N-[[(3S)-1-(p-Amidinophenyl)-2-oxo-3-pyrrolidinyl-carbamoyl]-β-alanine, ethyl ester), particularly the monoacetate and monoacetate hydrate forms thereof, as described in U.S. Pat. No. 5,484,946 assigned to Searle:

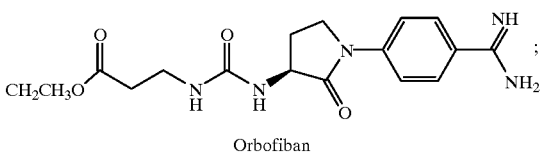

Orbofiban

Orbofiban

SB 214857 ((−)-(S)-2-[7-(4,4'-Bipiperidin-1-ylcarbonyl)-4-methyl-3-oxo-2,3,4,5-tetrahydro-1H-1,4-benzodiazepin-2-yl]acetic acid) from SmithKline Beecham, as described in WO 95/18619; ZD-2486 ((R)-3-Methyl-4-[4-[4-(4-pyridyl)piperazin-1-yl]phenoxy]butyric acid) from Zeneca, as described in U.S. Pat. Nos. 5,556,977 and 5,663,141; TAK-029 from Takeda; RPR 109891 from Rhone Polenc Rorer; GR144053 from Glaxo; GR233548 from Glaxo; and SDZ 562 from Sandoz.

The compounds MK-383, DMP 728, Ro44-9883, Ro43-8857, SC-54684 and GR144053 are described in Cook et al., *Drugs of the Future*, 1994, 19(2):135–159, and Cox et al., *Medicinal Research Reviews*, 1994, 14:195–228. DMP 728 is also described in *Circulation*, 1996,93:537–543; and GR144053 is also described in *Thrombosis and Hematosis*, 1993, 69:1071. TAK 029 is described in *J. Pharmacology and Experimental Therapeutics*, 1996,277:502–510. Xemlofiban is described in *Circulation*, 1995,92:2331.

More particularly, the GP IIb/IIIa receptor antagonist is selected from Compound A, Compound B, and DMP 754, which are all orally available compounds. Most particularly, the GP IIb/IIIa receptor antagonist is DMP 754.

One test which is used to evaluate IIb/IIIa receptor antagonist activity is based on evaluation of inhibition of ADP-stimulated platelets. Aggregation requires that fibrinogen bind to and occupy the platelet fibrinogen receptor site. Inhibitors of fibrinogen binding inhibit aggregation. In the ADP-stimulated platelet aggregation assay, human platelets are isolated from fresh blood, collected into acid citrate/dextrose by differential centrifugation followed by gel filtration on Sepharose 2B in divalent ion-free Tyrode's buffer (pH 7.4) containing 2% bovine serum albumin.

Platelet aggregation is measured at 37° C. in a Chronolog aggregometer. The reaction mixture contains gel-filtered human platelets (26×10$^8$ per ml), fibrinogen (100 micrograms per ml (ug/ml)), Ca$^{2+}$ (1 mM), and the compound to be tested. The aggregation is initiated by adding 10 mM ADP 1 minute after the other components are added. The reaction is then allowed to proceed for at least 2 minutes. The extent of inhibition of aggregation is expressed as the percentage of the rate of aggregation observed in the absence of inhibitor. The IC$_{50}$ is the dose of a particular compound inhibiting aggregation by 50% relative to a control lacking the compound.

Oral dosages of GP IIb/IIIa receptor antagonists when used for the indicated effects, will range between about 0.001 mg per kg of body weight per day (mg/kg/day) to about 50 mg/kg/day and preferably 0.005–20 mg/kg/day and most preferably 0.005–10 mg/kg/day. Suitable oral tablets and capsules contain between 0.1 mg and 5 g, preferably between 0.5 mg and 2 g, most preferably between 0.5 mg and 1 g, for example, 0.5 mg, 1 mg, 5 mg, 10 mg, 50 mg, 150 mg, 250 mg, or 500 mg of GP IIb/IIIa receptor antagonist. Oral administration may be in one or divided doses of two, three, or four times daily. A single daily dose is preferred.

Intravenously, the most preferred doses for GP IIb/IIIa receptor antagonists will range from about 0.5 μg to about 5 mg/kg/minute during a constant rate infusion, to achieve a plasma level concentration during the period of time of administration of between 0.1 ng/ml and 1 μg/ml.

Herein, the term antiplatelet agent (or inhibitor of platelet aggregation) is intended to include all pharmaceutically acceptable salt, ester and solvate forms, including hydrates, of compounds which have platelet aggregation inhibitory activity as well as pro-drug forms. Such pro-drugs are compounds which do not have platelet aggregation inhibitory activity outside the body but become active as inhibitors after they are administered to the patient. Therefore the use of such salts, esters solvate forms and pro-drugs of antiplatelet agents is included within the scope of this invention.

Likewise, the term GP IIb/IIIa receptor antagonist is intended to include all pharmaceutically acceptable salt, ester and solvate forms, including hydrates, of compounds which have GP IIb/IIIa receptor antagonist activity as well as pro-drug forms. Such pro-drugs are compounds which do not have GP IIb/IIIa receptor antagonist activity outside the body but become active as antagonists after they are administered to the patient. Therefore the use of such salts, esters, solvate forms and pro-drugs of GP IIb/IIIa receptor antagonists is also included within the scope of this invention. Pro-drug forms of IIb/IIIa receptor antagonists generally are not active antagonists until after they are metabolized in the body to the active drug form; such prodrugs may be, but are not limited to, ester derivatives. Ester derivatives of the described compounds may act as prodrugs which, when absorbed into the bloodstream of a warm-blooded animal, may cleave in such a manner as to release the drug form and permit the drug to afford improved therapeutic efficacy. An example of such a pro-drug is Ro 48-3657.

The compounds may have one or more chiral centers and the present compounds may occur as racemates, racemic mixtures and as individual diasteriomers or enantiomers with all such isomeric forms and mixtures thereof being included within the scope of this invention. Furthermore, some of the crystalline forms for compounds may exist as polymorphs and as such are intended to be included in the present invention. In addition, some of the compounds may form solvates with water or common organic solvents. Such solvates and hydrates, as well as anhydrous compositions, are encompassed within the scope of this invention. Some of the compounds described herein may contain olefinic double bonds, and unless specified otherwise, are meant to include both E and Z geometric isomers.

Other antiplatelet agents suitable for use in the present invention include clopidogrel (PLAVIX®, Bristol Myers Squibb) and ticlopidine (TICLID®, Roche Laboratories), both of which block ADP-induced platelet aggregation, as well as dipyridamole (PERSANTINE®, Boehringer Ingelheim), a platelet adhesion inhibitor, and aspirin.

Suitable oral formulations of clopidogrel may contain from 25 mg to 500 mg, preferably from 75 mg to 375 mg, and most preferably from 75 mg to 150 mg of clopidogrel. For example, the formulation may contain 25 mg, 50 mg, 75 mg, 150 mg, 250 mg, or 500 mg of clopidogrel. Oral administration may be in one or divided doses of two, three, or four times daily. A single daily dose is preferred. Dosage amounts for ticlopidine and for dipyridamole are described in the *Physicians' Desk Reference*. Dosage amounts of aspirin for the indicated effects are known to those skilled in medical arts, and generally range from about 75 mg to about 325 mg per day. For example, a formulation may contain 75 mg, 80 mg, 160 mg, 250 mg, or 325 mg of aspirin.

Combination

The instant pharmaceutical combinations comprising an antiplatelet agent in combination with a COX-2 inhibitor includes administration of a single pharmaceutical dosage formulation which contains both the antiplatelet agent and the COX-2 inhibitor, as well as administration of each active agent in its own separate pharmaceutical dosage formulation. Where separate dosage formulations are used, the antiplatelet agent and the COX-2 inhibitor can be administered at essentially the same time, i.e., concurrently, or at separately staggered times, i.e, sequentially. The "instant pharmaceutical combination" is understood to include all these regimens. Administration in these various ways are suitable for the present invention as long as the beneficial pharmaceutical effect of the antiplatelet agent and the COX-2 inhibitor are realized by the patient at substantially the same time. Such beneficial effect is preferably achieved when the target blood level concentrations of each active drug are maintained at substantially the same time. It is preferred that the antiplatelet agent and the COX-2 inhibitor be co-administered concurrently on a once-a-day dosing schedule; however, varying dosing schedules, such as the antiplatelet agent once per day and the COX-2 inhibitor once, twice or more times per day, is also encompassed herein. A single oral dosage formulation comprised of both an antiplatelet agent and the COX-2 inhibitor is preferred. A single dosage formulation will provide convenience for the patient, which is an important consideration especially for patients who already have coronary heart disease and may be in need of multiple medications.

It is expected that a combination therapy of intravenously administered GP IIb/IIIa receptor antagonist with orally administered COX-2 inhibitor could be used in response to an acute medical event where inhibition of platelet aggregation is needed, and may generally be administered for a period of time of one or two weeks or up to a month or longer if deemed necessary. Where the combination therapy involves for example oral administration of both the GP IIb/IIIa receptor antagonist and the COX-2 inhibitor, the therapy may be administered on a longer-term chronic basis, such as a period of several months or years, for as long as deemed medically appropriate for the patient.

The therapeutically effective amount is that amount of a drug or pharmaceutical agent that will elicit the biological or medical response of a tissue, a system, animal or human that is being sought by a researcher, veterinarian, medical doctor or other clinician. The prophylactically effective amount that amount of a pharmaceutical drug that will prevent or reduce the risk of occurrence of the biological or medical event that is sought to be prevented in a tissue, a system, animal or human by a researcher, veterinarian, medical doctor or other clinician. The dosage regimen utilizing an antiplatelet agent in combination with COX-2 inhibitor is selected in accordance with a variety of factors including type, species, age, weight, sex and medical condition of the patient; the severity of the condition to be treated; the route of administration; the renal and hepatic function of the patient; and the particular compound or salt or ester thereof employed. Since two different active agents are being used together in a combination therapy, the potency of each of the agents and the interactive effects achieved by combining them together must also be taken into account. A consideration of these factors is well within the purview of the ordinarily skilled clinician for the purpose of determining the therapeutically effective or prophylactically effective dosage amounts needed to prevent, counter, or arrest the progress of the condition.

Administration of the drug combination to the patient includes both self-administration and administration to the patient by another person.

Additional active agents may be used in combination with the COX-2 inhibitor and antiplatelet agent in a single dosage formulation, or may be administered to the patient in a separate dosage formulation, which allows for concurrent or sequential administration. Examples of additional active agents which may be employed include HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors; probucol; niacin; fibrates such as clofibrate, fenofibrate, and gemfibrizol; cholesterol absorption inhibitors; bile acid sequestrants; LDL (low density lipoprotein) receptor inducers; vitamin $B_6$ (also known as pyridoxine) and the pharmaceutically acceptable salts thereof such as the HCl salt; vitamin $B_{12}$ (also known as cyanocobalamin); β-adrenergic receptor blockers; folic acid or a pharmaceutically acceptable salt or ester thereof such as the sodium salt and the methylglucamine salt; and antioxidant vitamins such as vitamin C and E and beta carotene.

The active drugs can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active drugs may also be delivered by the use of monoclonal antibodies as individual carriers to which the compound molecules are coupled. They may also be coupled with soluble polymers as targetable drug carriers. Such polymers can include polyvinylpyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, the active drugs may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

Although the active agents may be administered in divided doses, for example two or three times daily, a single daily dose of each of the antiplatelet agent and the COX-2 inhibitor is preferred, with a single daily dose of both agents in a single pharmaceutical composition being most preferred.

The instant invention also encompasses a process for preparing a pharmaceutical composition comprising combining the antiplatelet agent and the COX-2 inhibitor with a pharmaceutically acceptable carrier, as well as the pharmaceutical composition which is made by combining the antiplatelet agent and the COX-2 inhibitor with a pharmaceutically acceptable carrier.

The compositions of this invention, and methods for administering the combination therapy of an antiplatelet agent with a COX-2 inhibitor, are useful for treating, preventing or reducing the risk of occurrence of acute coronary ischemic syndrome in mammals, and more particularly in humans, who are at risk of developing acute coronary ischemic syndrome. Acute coronary ischemic syndrome includes the conditions of unstable angina and non-Q-wave myocardial infarction.

Compositions and methods of the invention may be used to treat, prevent or reduce the risk of formation of thrombi and thromboemboli and therefore to prevent or reduce the risk of thrombotic occlusions and reocclusions. They are useful in surgery on peripheral arteries (arterial grafts, carotid endaterectomy) and in cardiovascular surgery where manipulation of arteries and organs, and/or the interaction of platelets with artificial surfaces, leads to platelet aggregation and potential formation of thrombi and thromboemboli. For example, the combination therapy can be used for preventing or reducing the risk of occurrence of platelet thrombosis, thromboembolism and reocclusion after acute intervention such as atherectomy, angioplasty, coronary artery bypass procedures or cardiac valve replacement. The combination therapy can also be used for preventing or reducing the risk of occurrence of platelet thrombosis, thromboembolism and reocclusion during and after thrombolytic therapy. Since blood vessels can also sustain chronic damage by the pathophysiological processes of atherosclerosis, patients with atherosclerosis can also be treated with the instant combination therapy to prevent or reduce the risk of occlusive thrombus formation. The instant combination therapy can be used to treat, prevent or reduce the risk of intermittent claudication, which is a clinical manifestation of peripheral vessel disease. Combination therapy of a COX-2 inhibitor with an antiplatelet agent may reduce the risk of thrombocytopenia.

The instant combination therapy can also be used to treat, prevent or reduce the risk of a first or subsequent Q-wave myocardial infarction in persons at risk for such events as well as to prevent or reduce the risk of restenosis in persons at risk for restenosis. Additionally, the instant combination therapy can be used for treating, preventing or reducing the risk of occurrence of acute cerebrovascular ischemic events (e.g. a first or subsequent thrombotic stroke, or transient ischemic attack). In general, the instant combination therapy can be used whenever antiplatelet therapy, or inhibition of platelet aggregation, is needed.

The compositions and methods of the present invention are also useful in combination with procedures for treating patients with other anticoagulants (e.g. thrombin inhibitors such as heparin and Factor Xa inhibitors such as warfarin), and thrombolytic agents (e.g. streptokinase and tissue plasminogen activator).

In accordance with this invention, a therapeutically effective amount of a COX-2 inhibitor and a therapeutically effective amount of an antiplatelet agent can be used for the preparation of a medicament useful for inhibiting platelet aggregation, and for treating, preventing or reducing the risk of developing acute coronary ischemic syndrome in mammals, particularly in humans. Additionally, a therapeutically effective amount of a COX-2 inhibitor and a therapeutically effective amount of an antiplatelet agent can be used for the preparation of a medicament useful for preventing or reducing the risk of formation of thrombi and thromboemboli, for preventing or reducing the risk of thrombotic occlusions and reocclusions, for treating, preventing or reducing the risk of a first or subsequent myocardial infarction, for preventing or reducing the risk of restenosis, for treating, preventing or reducing the risk of acute cerebrovascular ischemic events such as a first or subsequent thrombotic stroke or transient ischemic attack, and for halting or slowing the progression of atherosclerotic disease. More particularly, a therapeutically effective amount of a COX-2 inhibitor and a therapeutically effective amount of an antiplatelet agent can be used together for the preparation of a medicament suitable for oral administration which is useful for the above-described treatments. Similarly, a therapeutically effective amount of a COX-2 inhibitor can be used for the preparation of a medicament for use in combination with a therapeutically effective amount of an antiplatelet agent, which is useful for the above-described treatments. Also, a therapeutically effective amount of an antiplatelet agent can be used for the preparation of a medicament for use in combination with a therapeutically effective amount of a COX-2 inhibitor, which is useful for the above-described treatments.

An additional embodiment of the instant invention involves a kit comprised of a COX-2 inhibitor in an oral dosage formulation and an antiplatelet agent in a separate oral dosage formulation. More particularly, the kit is comprised of a COX-2 inhibitor selected from the group consisting of 5-chloro-3-(4-(methylsulfonyl)phenyl)-2-(2-methyl-5-pyridinyl)pyridine; 2-(3,5-difluorophenyl)-3-(4-(methylsulfonyl)phenyl)-2-cyclopenten-1-one; 3-phenyl-4-(4-(methylsulfonyl)phenyl)-2-(5H)-furanone; 3-(3,4-difluorophenyl)-4-(4-(methylsulfonyl)phenyl)-2-(5H)-furanone; 5,5-dimethyl-4-(4-(methylsulfonyl)phenyl)-3-(3-fluorophenyl)-5H-furan-2-one; and the antiplatelet agent is selected from the group consisting of a GP IIb/IIIa receptor antagonist, ticlopidine, clopidogrel, aspirin and dipyridamole. In one class of this embodiment the COX-2 inhibitor is selected from 5-chloro-3-(4-(methylsulfonyl) phenyl)-2-(2-methyl-5-pyridinyl)pyridine; 2-(3,5-difuuorophenyl)-3-(4-(methylsulfonyl)phenyl)-2-cyclopenten-1-one; 3-phenyl-4-(4-(methylsulfonyl)phenyl)-2-(5H)-furanone; 3-(3,4-difluorophenyl)-4-(4-(methylsulfonyl)phenyl)-2-(5H)-faranone; 5,5-dimethyl-4-(4-(methylsulfonyl)phenyl)-3-(3-fluorophenyl)-5H-furan-2-one, and more particularly the GP IIb/IIIa receptor antagonist is selected from Mpr-(Acetimidyl-Lys)-Gly-Asp-Trp-Phe-Cys-NH$_2$; Mpr-(Acetimidyl-Lys)-Gly-Asp-Trp-Phe-Pen-NH$_2$; Mpr-(Phenylimidyl-Lys)-Gly-Asp-Trp-Phe-Pen-NH$_2$; Mpr-(Phenylimidyl-Lys)-Gly-Asp-Trp-Phe-Cys-NH$_2$; N-Methyl-D-phenylalanyl-N-[(1S)-1-formyl-4-guanidinobutyl]-L-prolinamide; ((1-(2-((4-(aminoiminomethyl)benzoyl)amino)-3-(4-hydroxyphenyl)-1-oxopropyl)-4-piperidinyl)oxy)-(S)-acetic acid; N-(2-(2-(((3-((aminoiminomethyl)amino)-propyl)amino)carbonyl)-1-piperidnyl)-1-(cyclohexylmethyl)-2-oxoethyl)-(R,S)-glycine; Ethyl 3-[[4-[[4-(aminoiminomethyl)phenyl] amino]-1,4-dioxobutyl]amino]-4-pentynoate; (2-S-(n-Butylsulfonylamino)-3[4-(piperidin-4-yl)butyloxyphenyl] propionic acid hydrochloride; and 2(S)-[(p-Toluenesulfonyl)

amino]-3-[[[5,6,7,8-tetrahydro-4-oxo-5-[2-(piperidin-4-yl) ethyl]-4H-pyrazolo-[1,5-a][1,4]diazepin-2-yl]carbonyl]- amino]propionic acid. In a second class of this embodiment, the antiplatelet agent is a GP IIb/IIIa receptor antagonist selected from the group consisting of Compound A, Compound B, and DMP 754.

One example of this embodiment is a kit comprised of an oral dosage formulation of a COX-2 inhibitor and an oral dosage formulation of a GP IIb/IIIa receptor antagonist. The packaging for the kit could be designed and manufactured in a variety of ways. A preferred example is a blister package containing rows of a COX-2 inhibitor tablet and a GP IIb/IIIa receptor antagonist tablet placed side by side on the same blister card, each of the two tablets in its own blister bubble, with calendar or similar type markings on the card that convey to the user that one "pair" of tablets (i.e., one COX-2 inhibitor tablet and one GP IIb/IIIa receptor antagonist tablet) is to be ingested per day.

Examples of dosage formulations suitable for use in practicing the instant invention follow. In the examples, the COX-2 inhibitor is 3-phenyl-4-(4-(methylsulfonyl)phenyl)- 2-(5H)-furanone and the GP IIb/IIIa receptor antagonist is any one of [3(R)-[2-piperidin-4-yl)ethyl]-2-piperidone-1] acetyl-3(R)-methyl-β-alanine, 2(S)-[(p-Toluenesulfonyl) amino]-3-[[[5,6,7,8-tetrahydro-4-oxo-5-[2-(piperidin-4-yl) ethyl]-4H-pyrazolo-[1,5-a][1,4]diazepin-2-yl]carbonyl]- amino]propionic acid, or ((R)-methyl-3-[[[3-[4- (aminoiminomethyl)phenyl]-4,5-dihydro-5-isoxazolyl] acetyl]amino]-N-(butoxycarbonyl)-L-alanine monoacetate.

EXAMPLE 1

Tablet Preparation

Tablets containing 25.0, 50.0, and 100.0 mg, respectively, of a GP IIb/IIIa receptor antagonist are prepared as illustrated below:

| TABLE FOR DOSES CONTAINING FROM 25–100 MG OF GP IIB/IIIA RECEPTOR ANTAGONIST | | | |
|---|---|---|---|
| | Amount-mg | | |
| GP IIb/IIIa receptor antagonist | 25.0 | 50.0 | 100.0 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 2

Intravenous formulations

An intravenous dosage form of the GP IIb/IIIa receptor antagonist is prepared as follows:

| | Amount |
|---|---|
| GP IIb/IIIa receptor antagonist | 0.5–10.0 mg |
| Sodium Citrate | 5–50 mg |
| Citric Acid | 1–15 mg |
| Sodium Chloride | 1–8 mg |
| Water for Injection (USP) | q.s. to 1 L |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md., copyright 1994.

EXAMPLE 3

| Wet granulated tablet composition | |
|---|---|
| Amount per tablet | Ingredient |
| 25 mg | COX-2 Inhibitor |
| 79.7 mg | Microcrystalline cellulose |
| 79.7 mg | Lactose monohydrate |
| 6 mg | Hydroxypropyl cellulose |
| 8 mg | Croscarmellose sodium |
| 0.6 mg | Iron oxide |
| 1 mg | Magnesium stearate |

Tablet dose strengths of between 5 and 125 mg can be accommodated by varying total tablet weight, and the ratio of the first three ingredients. Generally it is preferable to maintain a 1:1 ratio for microcrystalline cellulose: lactose monohydrate.

EXAMPLE 3a

| Wet granulated tablet composition | |
|---|---|
| Amount per tablet | Ingredient |
| 12.5 mg | COX-2 Inhibitor |
| 86 mg | Microcrystalline cellulose |
| 86 mg | Lactose monohydrate |
| 6 mg | Hydroxypropyl cellulose |
| 8 mg | Croscarmellose sodium |
| 0.6 mg | Iron oxide |
| 1 mg | Magnesium stearate |

EXAMPLE 3b

| Wet granulated tablet composition | |
|---|---|
| Amount per tablet | Ingredient |
| 10 mg | COX-2 Inhibitor |
| 87.2 mg | Microcrystalline cellulose |
| 87.2 mg | Lactose monohydrate |
| 6 mg | Hydroxypropyl cellulose |
| 8 mg | Croscarmellose sodium |

-continued

Wet granulated tablet composition

| Amount per tablet | Ingredient |
|---|---|
| 0.6 mg | Iron oxide |
| 1 mg | Magnesium stearate |

EXAMPLE 3c

Wet granulated tablet composition

| Amount per tablet | Ingredient |
|---|---|
| 5 mg | COX-2 Inhibitor |
| 89.7 mg | Microcrystalline cellulose |
| 89.7 mg | Lactose monohydrate |
| 6 mg | Hydroxypropyl cellulose |
| 8 mg | Croscarmellose sodium |
| 0.6 mg | Iron oxide |
| 1 mg | Magnesium stearate |

EXAMPLE 4

Directly compressed tablet composition

| Amount per tablet | Ingredient |
|---|---|
| 25 mg | COX-2 Inhibitor |
| 106.9 mg | Microcrystalline cellulose |
| 106.9 mg | Lactose anhydrate |
| 7.5 mg | Croscarmellose sodium |
| 3.7 mg | Magnesium stearate |

Tablet dose strengths of between 5 and 125 mg can be accommodated by varying total tablet weight, and the ratio of the first three ingredients. Generally it is preferable to maintain a 1:1 ratio for microcrystalline cellulose:lactose monohydrate.

EXAMPLE 4a

Directly compressed tablet composition

| Amount per tablet | Ingredient |
|---|---|
| 12.5 mg | COX-2 Inhibitor |
| 113.2 mg | Microcrystalline cellulose |
| 113.2 mg | Lactose anhydrate |
| 7.5 mg | Croscarmellose sodium |
| 3.7 mg | Magnesium stearate |

EXAMPLE 4b

Directly compressed tablet composition

| Amount per tablet | Ingredient |
|---|---|
| 10 mg | COX-2 Inhibitor |
| 42.5 mg | Microcrystalline cellulose |

-continued

Directly compressed tablet composition

| Amount per tablet | Ingredient |
|---|---|
| 42.5 mg | Lactose anhydrate |
| 4 mg | Croscarmellose sodium |
| 1 mg | Magnesium stearate |

EXAMPLE 4c

Directly compressed tablet composition

| Amount per tablet | Ingredient |
|---|---|
| 5 mg | COX-2 Inhibitor |
| 45 mg | Microcrystalline cellulose |
| 45 mg | Lactose anhydrate |
| 4 mg | Croscarmellose sodium |
| 1 mg | Magnesium stearate |

EXAMPLE 5

Hard gelatin capsule composition

| Amount per capsule | Ingredient |
|---|---|
| 25 mg | COX-2 Inhibitor |
| 37 mg | Microcrystalline cellulose |
| 37 mg | Lactose anhydrate |
| 1 mg | Magnesium stearate |
| 1 capsule | Hard gelatin capsule |

Capsule dose strengths of between 1 and 50 mg can be accommodated by varying total fill weight, and the ratio of the first three ingredients. Generally it is preferable to maintain a 1:1 ratio for microcrystalline cellulose:lactose monohydrate.

EXAMPLE 6

Oral solution

| Amount per 5 mL dose | Ingredient |
|---|---|
| 50 mg | COX-2 Inhibitor |
| to 5 mL with Polyethylene oxide 400 | |

Solution dose strengths of between 1 and 50 mg/5 mL can be accommodated by varying the ratio of the two ingredients.

EXAMPLE 7

Oral suspension

| Amount per 5 mL dose | Ingredient |
|---|---|
| 101 mg | COX-2 Inhibitor |
| 150 mg | Polyvinylpyrrolidone |

-continued

Oral suspension

| Amount per 5 mL dose | Ingredient |
|---|---|
| 2.5 mg | Poly oxyethylene sorbitan monolaurate |
| 10 mg | Benzoic acid |
| to 5 mL with sorbitol solution (70 %) | |

Suspension dose strengths of between 1 and 50 mg/5 ml can be accommodated by varying the ratio of the first two ingredients.

EXAMPLE 8

Intravenous infusion

| Amount per 200 mL dose | Ingredient |
|---|---|
| 1 mg | COX-2 inhibitor |
| 0.2 mg | Polyethylene oxide 400 |
| 1.8 mg | Sodium chloride |
| to 200 mL | Purified water |

EXAMPLE 9

Combination Tablet Preparation

Tablets containing 25.0, 50.0, and 100.0 mg, respectively, of a GP IIb/IIIa receptor antagonist and 25 mg COX-2 Inhibitor are prepared as illustrated below:

TABLE FOR DOSES CONTAINING
FROM 25–100 MG OF GP IIB/IIIA RECEPTOR ANTAGONIST
AND 25 MG COX-2 INHIBITOR

| | Amount-mg | | |
|---|---|---|---|
| GP IIb/IIIa receptor antagonist | 25.0 | 50.0 | 100.0 |
| COX-2 Inhibitor | 25.0 | 25.0 | 25.0 |
| Microcrystalline cellulose | 37.25 | 100.0 | 175.0 |
| Modified food corn starch | 37.25 | 4.25 | 8.5 |
| Magnesium stearate | 0.50 | 0.75 | 1.5 |

Both active compounds, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of GP IIb/IIIa receptor antagonist per tablet, and 25 mg COX-2 inhibitor, per tablet.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the active agents used in the instant invention as indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method for treating a condition selected from the group consisting of acute coronary ischemic syndrome, thrombosis, thromboembolism, thrombotic occlusion and reocclusion, transient ischemic attack, and first or subsequent thrombotic stroke, in a patient having the condition, comprising administering to the patient a therapeutically effective amount of an antiplatelet agent in combination with 0.05 to 10 mg/kg/day of a COX-2 inhibitor.

2. The method of claim 1 wherein the antiplatelet agent is a glycoprotein IIb/IIIa receptor antagonist or a pharmaceutically acceptable salt thereof.

3. A method of claim 1, wherein the acute coronary ischemic syndrome is selected from the group consisting of angina pectoris, first Q-wave myocardial infarction, and subsequent Q-wave myocardial infarction.

4. The method of claim 1 wherein the COX-2 inhibitor is selected from:
5,5-dimethyl-4-(4-(methylsulfonyl)phenyl)-3-(2-propoxy)-5H-furan-2-one;
5-chloro-3-(4-(methylsulfonyl)phenyl)-2-(2-methyl-5-pyridinyl)pyridine;
2-(3,5-difluorophenyl)-3-(4-(methylsulfonyl)phenyl)-2-cyclopenten-1-one;
5(S)-5-ethyl-5-methyl-4-(4-(methylsulfonyl)phenyl)-3-(2-propoxy)-5H-furan-2-one;
5-ethyl-5-methyl-4-(4-(methylsulfonyl)phenyl)-3-(3,4-difluorophenyl)-5H-furan-2-one;
3-((2-thiazolyl)methoxy)-4-(4-(methylsulfonyl)phenyl)-5,5-dimethyl-5H-furan-2-one;
3-propyloxy-4-(4-(methylsulfonyl)phenyl)-5,5-dimethyl-5H-furan-2-one;
3-(1-cyclopropylethoxy)-5,5-dimethyl-4-(4-methylsulfonyl)phenyl)-5H-furan-2-one;
sodium 2-(4-chlorophenyl)-3-(4-(methylsulfonyl)phenyl)-4-oxo-2-pentenoate;
3-(cyclopropylmethoxy)-5,5-dimethyl-4-(4-(methylsulfonyl)phenyl)-5H-furan-2-one;
3-(cyclopropylmethoxy)-5,5-dimethyl-4-(4-(methylsulfonyl)phenyl)-2,5-dihydrofuran-2-ol;
3-isopropoxy-5,5-dimethyl-4-(4-(methylsulfonyl)phenyl)-2,5-dihydrofuran-2-ol;
5,5-Dimethyl-3-(3-fluorophenyl)-2-hydroxy-4-(4-(methylsulfonyl)phenyl)-2,5-dihydrofuran;
5-Chloro-3-(4-(methylsulfonyl)phenyl)-2-(3-pyridinyl)pyridine;
3-phenyl-4-(4-(methylsulfonyl)phenyl)-2-(5H)-furanone;
3-(3,4-difluorophenyl)-4-(4-(methylsulfonyl)phenyl)-2-(5H)-furanone;
5,5-dimethyl-4-(4-(methylsulfonyl)phenyl)-3-(3-fluorophenyl)-5H-furan-2-one;
or a pharmaceutically acceptable salt thereof.

5. The method of claim 4 wherein the COX-2 inhibitor is selected from:
5-chloro-3-(4-(methylsulfonyl)phenyl)-2-(2-methyl-5-pyridinyl)pyridine;
2-(3,5-difluorophenyl)-3-(4-(methylsulfonyl)phenyl)-2-cyclopenten-1-one;
3-phenyl-4-(4-(methylsulfonyl)phenyl)-2-(5H)-furanone;
3-(3,4-difluorophenyl)-4-(4-(methylsulfonyl)phenyl)-2-(5H)-furanone;

5,5-dimethyl-4-(4-(methylsulfonyl)phenyl)-3-(3-fluorophenyl)-5H-furan-2-one;
or a pharmaceutically acceptable salt thereof.

6. The method of claim 5 wherein the COX-2 inhibitor is 5-chloro-3-(4-(methylsulfonyl)phenyl)-2-(2-methyl-5-pyridinyl)pyridine or a pharmaceutically acceptable salt thereof.

7. The method of claim 5 wherein the COX-2 inhibitor is 2-(3,5-difluorophenyl)-3-(4-(methylsulfonyl)phenyl)-2-cyclopenten-1-one or a pharmaceutically acceptable salt thereof.

8. The method of claim 5 wherein the COX-2 inhibitor is 3-phenyl-4-(4-(methylsulfonyl)phenyl)-2-(5H)-furanone or a pharmaceutically acceptable salt thereof.

9. The method of claim 5 wherein the COX-2 inhibitor is 3-(3,4-difluorophenyl)-4-(4-(methylsulfonyl)phenyl)-2-(5H)-furanone or a pharmaceutically acceptable salt thereof.

10. The method of claim 5 wherein the COX-2 inhibitor is 5,5-dimethyl-4-(4-(methylsulfonyl)phenyl)-3-(3-fluorophenyl)-5H-furan-2-one or a pharmaceutically acceptable salt thereof.

11. The method of claim 1 wherein the antiplatelet agent is selected from the group consisting of a glycoprotein IIb/IIIa receptor antagonist, ticlopidine, clopidogrel, dipyridamole and aspirin.

12. The method of claim 11 wherein the antiplatelet agent is a glycoprotein IIb/IIIa receptor antagonist selected from Mpr-(Acetimidyl-Lys)-Gly-Asp-Trp-Phe-Cys-$NH_2$; Mpr-(Acetimidyl-Lys)-Gly-Asp-Trp-Phe-Pen-$NH_2$; Mpr-(Phenylimidyl-Lys)-Gly-Asp-Trp-Phe-Pen-$NH_2$; Mpr-(Phenylimidyl-Lys)-Gly-Asp-Trp-Phe-Cys-$NH_2$; N-Methyl-D-phenylalanyl-N-[(1S)-1-formyl-4-guanidinobutyl]-L-prolinamide; ((1-(2-((4-(aminoiminomethyl)benzoyl)amino)-3-(4-hydroxyphenyl)-1-oxopropyl)-4-piperidinyl)oxy)-(S)-acetic acid; N-(2-(2-(((3-((aminoiminomethyl)amino)-propyl)amino)carbonyl)-1-piperidnyl)-1-(cyclohexylmethyl)-2-oxoethyl)-(R,S)-glycine; Ethyl 3-[[4-[[4-(aminoiminomethyl)phenyl]amino]-1,4-dioxobutyl]amino]-4-pentynoate; (2-S-(n-Butylsulfonylamino)-3[4-(piperidin-4-yl)butyloxyphenyl]propionic acid hydrochloride; and 2(S)-[(p-Toluenesulfonyl)amino]-3-[[[5,6,7,8-tetrahydro-4-oxo-5-[2-(piperidin-4-yl)ethyl]-4H-pyrazolo-[1,5-a][1,4]diazepin-2-yl]carbonyl]-amino] propionic acid; [3(R)-[2-piperidin-4-yl)ethyl]-2-piperidone-1]acetyl-3(R)-methyl-β-alanine; and ((R)-methyl-3-[[[3-[4-(aminoiminomethyl)phenyl]-4,5-dihydro-5-isoxazolyl] acetyl]amino]-N-(butoxycarbonyl)-L-alanine monoacetate, or a pharmaceutically acceptable salt, ester or pro-drug thereof.

13. A method of claim 11, wherein the antiplatelet agent is selected from the group consisting of ticlopidine, clopidogrel, dipyridamole and aspirin.

14. A method for the prophylaxis of a condition selected from the group consisting of acute coronary ischemic syndrome, thrombosis, thromboembolism, thrombotic occlusion and reocclusion, transient ischemic attack, and first or subsequent thrombotic stroke, in a patient, comprising administering to a patient at increased risk there for a prophylactically effective amount of an antiplatelet agent in combination with 0.05 to 10 mg/kg/day of a COX-2 inhibitor.

15. A method for reducing the risk of developing a condition selected from the group consisting of acute coronary ischemic syndrome, thrombosis, thromboembolism, thrombotic occlusion and reocclusion, transient ischemic attack, and first or subsequent thrombotic stroke, in a patient at risk to developing the condition, comprising administering to the patient a therapeutically effective amount of an antiplatelet agent in combination with 0.05 to 10 mg/kg/day of a COX-2 inhibitor.

* * * * *